United States Patent [19]
Beshouri et al.

[11] Patent Number: 5,631,400
[45] Date of Patent: May 20, 1997

[54] CARBONYLATION PROCESS

[75] Inventors: Sharon M. Beshouri; Tonya L. Garcia, both of Houston, Tex.

[73] Assignee: Shell Oil Company, Houston, Tex.

[21] Appl. No.: 574,822

[22] Filed: Dec. 19, 1995

[51] Int. Cl.$^6$ ............................................. C07C 69/52
[52] U.S. Cl. ............................................. 560/207; 562/522
[58] Field of Search ............................ 560/207; 562/522

[56]  References Cited

U.S. PATENT DOCUMENTS

| | | | |
|---|---|---|---|
| 4,940,787 | 7/1990 | Drent | 536/124 |
| 5,099,062 | 3/1992 | Drent et al. | 560/207 |

FOREIGN PATENT DOCUMENTS

| | | |
|---|---|---|
| 0186228A1 | 7/1986 | European Pat. Off. . |
| 0495547A2 | 7/1992 | European Pat. Off. . |

OTHER PUBLICATIONS

S. A. Miller, "Acetylene: Properties Manufacture and Uses", vol. 1, Ernest Benn Ltd., London (1965).

*Primary Examiner*—Paul J. Killos
*Attorney, Agent, or Firm*—Del S. Christensen

[57]  ABSTRACT

A process is provided for carbonylation of ethylenic unsaturation comprising the steps of: providing a catalyst system comprising a) a Group VIII metal compound, b) an organic phosphine, and c) and acid; and contacting acetylene, the catalyst system, carbon monoxide, hydrogen, and a nucleophilic compound under conditions effective to carbonylate the acetylene. The presents of hydrogen unexpectedly improves the yield of the desired product (i.e., acrylic acid or the ester thereof).

12 Claims, No Drawings

CARBONYLATION PROCESS

FIELD OF THE INVENTION

This invention relates to a process for the carbonylation of acetylene by reaction with carbon monoxide and a nucleophilic compound in the presence of a Group VIII metal and hydrogen.

BACKGROUND OF THE INVENTION

EP-A-495547 describes reactions in which optionally substituted olefinically unsaturated compounds are reacted with carbon monoxide and a co-reactant in the presence of a catalyst system comprising a source of palladium-cations, a source of specific aliphatic bidentate diphosphines and a source of anions. The co-reactant of EP-A-495547 is, in the terminology of the present invention, the nucleophilic component. A variety of products are also described in the patent. These products are produced in accordance with disclosed carbonylation reactions depending upon the reactants, the prevailing reaction conditions and the selected catalyst system. The relative amounts of co-reactants, the composition of the diphosphine ligand and on the source of anions also greatly enhances or suppresses the production of these varying products.

While one skilled in the art can generally obtain desired products in reasonably good yields based on the teachings of EP-A-495547 and EP-186,228A1, it would be desirable to improve yields based on catalyst usage. This greatly effects the commercial viability of these methods. Accordingly, improving such yields without impeding such factors as selectivity, reaction rates, and catalyst stability continues to be a highly sought goal.

It is therefore an object of this invention to provide a process for the carbonylation of acetylene by the reaction of carbon monoxide and a nucleophilic compound to for acrylic acid or an ester thereof.

It is a further object of this invention to provide a carbonylation reaction with an improved rate of reaction or yield based on catalyst over prior art processes.

It is a yet further object of this invention to provide a catalyst system for the carbonylation of acetylene the reaction of carbon monoxide and a nucleophilic compound with the presence of hydrogen.

SUMMARY OF THE INVENTION

In accordance with this invention, a process is provided for the carbonylation of ethylenically unsaturated compounds, the process comprising the steps of:

providing a catalyst system comprising
  a) a Group VIII metal compound,
  b) an organic phosphine,
  c) an acid; and
contacting acetylene, the catalyst system, carbon monoxide, hydrogen, and a nucleophilic compound under conditions effective to carbonylate the acetylene.

A hydrogen partial pressure during the carbonylation reaction, under many conditions, increases the yield of carbonylation products and/or increases the rate of the carbonylation reaction. It is unexpected that the presence of hydrogen would increase the yield of acrylic acid (or the ester thereof, depending on the nucleophilic agent used) rather than to cause products such as acrolein or propionaldehyde to result.

It is preferred that hydrogen be present in the practice of the present invention in a partial pressure of at least 50 psig and preferably between about 100 and about 1000 psi.

DETAILED DESCRIPTION OF THE INVENTION

The catalyst system of the present invention may be provided with a Group VIII metal ion, and an organic phosphine according to, for example, either U.S. Pat. No. 4,940,787 or U.S. Pat. No. 5,099,062. Such references do not suggest any advantage to performing the carbonylation reaction in the presence of hydrogen wherein the hydrogen is not a reactant.

The Group VIII metal compounds may be cations that originate from salts. For example, Group VIII metal salts derived from nitric acid have been found useful in this regard. Additionally, Group VIII metal salts derived from sulfuric acid, and sulfonic acids, such as p-toluenesulfonic acid, methanesulfonic acid or trifluoromethane sulfonic acid can be used as Group VIII metal cation sources. Preferably, a Group VIII metal salt of a carboxylic acid such as acetic acid, trifluoro acetic acid, or propionic acid is utilized.

It is also possible to employ a Group VIII metal source such as the metallic element itself or a zero valence Group VIII metal complex. Such a zero valence complex can be used with carbon monoxide, for example.

Palladium is the preferred Group VIII metal in the practice of the present invention, and palladium diacetate is an acceptable source of the palladium cation.

The catalyst system of the present invention preferably also includes a protonic acid. The protonic acid provides a source of protons.

The amount of acid incorporated in the catalyst system of the present invention can be between about one and about one thousand mmoles per mmole of Group VIII metal. More preferably, between about fifty and about five hundred mmoles of acid per mmole of the Group VIII metal are provided. Acceptable acids include, for example, trifluoromethane sulfonic acid, methane sulfonic acid, p-toluene sulfonic acid, and trifluoroacetic acid, which are referred to as super acids. Super acids have been defined as acids or acid media which have a proton donating ability equal to or greater than 100% anhydrous sulfuric acid. The strength of the acids of the present inventions (their $pK_a$'s) are measured in aqueous solution at one atmosphere pressure and 25° C.

Acid strength is defined as the ability of a compound to give up or donate a proton. Base strength, conversely, is the ability to accept a proton. When an acid gives up a proton, a conjugate base is formed. The conjugate of a strong acid is a weak base.

A number of organic phosphines are known and acceptable in the practice of the present invention. Suitable organic phosphines are disclosed in, for example, European Patent Application No. 0 186 228 A1, the disclosure of which is incorporated herein by reference. Generally, organic phosphines that are know to be effective in carbonylation catalyst systems are useful in the practice of the present invention.

The ratio of moles of organic phosphines to moles of Group VIII metal is preferably in the range of from 1.0 to 1000. The most preferred range is from 50 to 500 moles of organic phosphines per gram atom of Group VIII metal.

Conveniently, the amount of catalyst system used in this invention is relatively small. Preferred amounts are in the range of 10-7 to 10-1 gram atom of Group VIII metal per mole of ethylenically unsaturated compound. A more preferred range is from 10-6 to 10-2 gram atom of Group VIII metal per mole of unsaturated compound.

Suitable nucleophilic components useful in the process of the present invention include compounds comprising a nucleophilic moiety and a mobile hydrogen atom. Examples are mono- and dihydric alkanols. Water, methanol, ethanol, n-butanol, ethylene glycol, isopropanol, butanediols and hexanol-1, and amines, such as ethylamine and diethylamine are also examples of such moieties. Alkanols having from one to six carbon atoms, and alkanediols having from two to six carbon atoms are preferred. n-Butanol-1, methanol and 1,4-butanediol are especially preferred as nucleophilic components. These nucleophilic components enable the production of valuable carbonylation products such as acrylic acid and acrylic acid esters. These products are of considerable commercial interest given their use in solvents and in flavoring compositions and perfumes.

In the process of this invention, the ethylenically unsaturated compound or the nucleophilic compound may be used in excess and may accordingly serve as a solvent during the reaction. It is also possible to perform the reaction in the presence of an additional liquid diluent. This is particularly the case when the reactants are used in stoichiometric amounts. Suitable diluents are, for example, polar aprotic compounds such as ketones or ethers. Preferred diluents are tetrahydrofuran and the dimethylether of diethyleneglycol (diglyme).

Acetylene is typically contacted with the catalyst system, hydrogen and carbon monoxide according to the present invention as a saturated solution of acetylene in a solvent such as acetone, N-methyl pyrrolidinone, dimethyl formamide, diglyme. Acceptable solvents for acetylene are known in the art from, for example, S. A. Miller, *Acetylene: Properties, Manufacture and Uses*, Vol. 1, Ernest Benn Ltd., London (1965).

Further reaction promoters, such as drying agents and/or antioxidants, may also be used in the process of this invention. Suitable drying agents include acetals, such as dimethyl-acetal of acetone, ketals and the like. A preferred drying agent is trimethyl orthoformate. Typical antioxidants include quinones, hydroquinones, and alkyl substituted hydroquinones such and methyl hydroquinone.

The carbonylation reaction of the present invention may be carried out at moderate temperatures. Generally, a range between 30° and 200° C. is used. A preferred range is from 50° to 150° C. Reaction pressures may be atmospheric or superatmospheric. In particular pressures in the range of from 5 to 70 bar (75 to 1030 psig) are preferred. Higher pressures are not precluded but usually do not provide advantages.

The hydrogen of the present invention is preferably provided by supplying carbon monoxide reactant as a mixture of hydrogen and carbon monoxide. Carbon monoxide is often available as a synthesis gas, in which a significant fraction of the stream is hydrogen. Such mixture of carbon monoxide and hydrogen can be, for example, half hydrogen and half carbon monoxide. The partial pressure of hydrogen during the carbonylation of the present invention is preferably between about 5 psi and about 1000 psi. The carbonylation of the present invention is preferably performed wherein a vapor phase is present wherein a ratio of hydrogen to carbon monoxide is between about 1:10 and about 10:1, and more preferably between 1:2 and 2:1.

The invention will be illustrated by the following non-limiting examples.

EXAMPLES

Thirty-one sets of carbonylation runs were made, one on each set with no hydrogen present and one of each set with a pressure applied to the reaction mixture by a gas having a composition of 50% hydrogen and 50% carbon monoxide. For each run, a 500 ml autoclave was charged with a catalyst solution containing 20 grams of acetone, palladium acetate, trifluoromethane sulfonic acid, and 0.4 grams of diphenyl (2-pyridyl) phosphine and 0.3 grams of an anti-oxidant (methyl hydroquinone). To the reactor was added 100 grams of dimethylketone (DMK) saturated with acetylene. The reactor was closed and either the carbon monoxide or the carbon monoxide-hydrogen mixture was added to a target pressure. Ten or fifteen ml of water was added by a syringe pump and the reactor was heated to a target temperature. After three hours the reactor was cooled, the gas was vented and acrylic acid was separated from the reactor contents. The Table below lists the yield of acrylic acid obtained in each experiment, along with the amounts of water, palladium, and acid and temperature and pressure.

TABLE

CENTRAL COMPOSITE DESIGN RESULTS: CO

| Run No. | Water (ml) | Temp. (°C.) | Press (psig) | L/H+ | MolAA/ molPD w/o $H_2$ | MolAA/ molPd with $H_2$ |
|---|---|---|---|---|---|---|
| 1 | 10 | 40 | 500 | 100/100 | 7558 | 11031 |
| 2 | 15 | 40 | 500 | 200/100 | 6539 | 8259 |
| 3 | 15 | 40 | 500 | 100/200 | 8932 | 10805 |
| 4 | 10 | 40 | 500 | 200/200 | 6874 | 17982 |
| 5 | 15 | 40 | 750 | 100/100 | 9833 | 12587 |
| 6 | 10 | 40 | 750 | 200/100 | 4097 | 4587 |
| 7 | 10 | 40 | 750 | 100/200 | 7682 | 15807 |
| 8 | 15 | 40 | 750 | 200/200 | 8874 | 11049 |
| 9 | 15 | 65 | 500 | 100/100 | 8611 | 11739 |
| 10 | 10 | 65 | 500 | 200/100 | 372 | 5219 |
| 11 | 10 | 65 | 500 | 100/200 | 11415 | 10679 |
| 12 | 15 | 65 | 500 | 200/200 | 3766 | 12966 |
| 13 | 10 | 65 | 750 | 100/100 | 11952 | 14714 |
| 14 | 15 | 65 | 750 | 200/100 | 7473 | 2051 |
| 15 | 15 | 65 | 750 | 100/200 | 9464 | 8840 |
| 16 | 10 | 65 | 750 | 200/200 | 12456 | 1865 |
| 17 | 10 | 27.5 | 625 | 150/150 | 5288 | 14507 |
| 18 | 10 | 77.5 | 625 | 150/150 | 11632 | 13372 |
| 19 | 10 | 52.5 | 375 | 150/150 | 10512 | 14833 |
| 20 | 10 | 52.5 | 875 | 150/150 | 13101 | 12165 |
| 21 | 10 | 52.5 | 625 | 150/50 | 1682 | 5865 |
| 22 | 10 | 52.5 | 625 | 150/250 | 11621 | 16804 |
| 23 | 10 | 52.5 | 625 | 50/150 | 7161 | 12455 |
| 24 | 10 | 52.5 | 625 | 250/150 | 5736 | 11562 |
| 25 | 15 | 52.5 | 625 | 150/150 | 5104 | 16718 |
| 26 | 10 | 52.5 | 625 | 150/150 | 7601 | 17106 |
| 27 | 10 | 52.5 | 625 | 150/150 | 8830 | 17088 |
| 28 | 10 | 52.5 | 625 | 150/150 | 7725 | 13987 |
| 29 | 10 | 52.5 | 625 | 150/150 | 10638 | 11764 |
| 30 | 10 | 52.5 | 625 | 150/150 | 10140 | 13295 |
| 31 | 10 | 52.5 | 625 | 150/150 | 8447 | 12052 |

The product from representative runs was tested for hydrogenation by-products such as acrolein and propionaldehyde, and none was found.

From the Table, it can be seen that, under most conditions, the comparable run with hydrogen present resulted in a greater yield of acrylic acid. This is especially surprising in light of the fact that the comparable run with hydrogen present had only half of the partial pressure of carbon monoxide. Further, the best runs in which the hydrogen was present achieved a higher yield than the best runs without hydrogen. This is particularly surprising considering the possibility of competing reactions that would decrease yields of acrylic acid.

We claim:

1. A process for carbonylation of ethylenic unsaturation comprising the steps of:
   providing a catalyst system comprising
   a) a Group VIII metal compound,
   b) an organic phosphine, and
   c) an acid; and
   contacting acetylene, the catalyst system, carbon monoxide, hydrogen, and a nucleophilic compound under conditions effective to carbonylate the acetylene.

2. The process of claim 1 wherein the hydrogen is present with a partial pressure of at least 50 psi.

3. The process of claim 2 wherein the hydrogen is present with a partial pressure of between about 100 and about 1000 psi.

4. The process of claim 1 wherein the conditions effective to carbonylate the acetylene comprise a temperature greater than about 75° C. and a total pressure greater than about 1100 psig.

5. The process of claim 1 wherein the Group VIII metal is palladium.

6. The process of claim 1 wherein the nucleophilic compound is water, and the carbonylated product is acrylic acid.

7. The process of claim 1 wherein the nucleophilic compound is an alcohol, and the carbonylated product is an acrylate ester.

8. The process of claim 2 wherein the palladium compound comprises palladium acetate.

9. The process of claim 1 wherein the organic phosphine comprises diphenyl (2-pyridyl) phosphine.

10. The process of claim 1 wherein the catalyst system further comprises an antioxidant.

11. The process of claim 10 wherein the antioxidant comprises methyl hydroquinone.

12. The process of claim 10 wherein the carbon monoxide is contacted with the acetylene, catalyst system, and nucleophilic compound with a partial pressure of between about 100 and about 1000 psi, and the hydrogen is present with a partial pressure of between about 100 and about 1000 psi.

* * * * *